US00PP09864P

United States Patent [19]

Zaiger et al.

[11] Patent Number: Plant 9,864

[45] Date of Patent: Apr. 22, 1997

[54] APRICOT TREE "AUTUMN GLOW"

[76] Inventors: Chris F. Zaiger, 929 Grimes Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 596,711

[22] Filed: Feb. 5, 1996

[51] Int. Cl.[6] ..... A01H 5/00

[52] U.S. Cl. ..... Plt./39

*Primary Examiner*—James R. Feyrer

[57] ABSTRACT

A new and distinct variety of apriocot, *Prunus armeniaca* tree with the following combination of unique features that are outstanding in a new variety:

1. Late maturity of yellow flesh fruit.
2. Heavy and regular production.
3. Fruit with good flavor and eating quality.
4. Fruit with firm flesh, good handling and shipping quality.
5. Vigorous, semi-spreading growth.
6. Relatively uniform ripening of fruit throughout the tree.
7. Fruit with a high degree of soluble solids (average 16% Brix).

1 Drawing Sheet

ORIGIN OF THE VARIETY

The present new and distinct apricot tree was originated by us in our experimental orchard located near Modesto, Calif., as an open pollinated seedling selection from a seedling, field identification number 6EC35. The seedling (field identification number 6EC35) originated from open pollinated Tri-Gems Apricot (U.S. Plant Pat. No. 6,755) seeds. We grew and maintained a large group of these open pollinated seedlings under careful observation, during which time one late maturing seedling having especially desirable fruit characteristics, which is the present variety, was selected for asexual reproduction and commercialization.

ASEXUAL REPRODUCTION OF THE VARIETY

Asexual reproduction of the new and distinct variety of apricot tree was accomplished by budding, as performed by us in our experimental orchard located near Modesto, Calif. and shows that all characteristics are established and transmitted through succeeding asexual propagations and run true to the original tree in all respects.

SUMMARY OF THE VARIETY

The present new and distinct apricot tree is of large size, vigorous, semi-spreading growth, and a regular and productive bearer of large, firm, yellow flesh, freestone fruit with good flavor and eating quality. The fruit is further characterized by being relatively uniform in maturity throughout the tree, having a high degree of soluble solids (average 16% Brix), having the ability to ship to long distance markets and, in comparison to the fruit from Tri-Gems Apricot (U.S. Plant Pat. No. 6,755) variety, the fruit is approximately two months later in maturity.

DESCRIPTION OF THE PHOTOGRAPH

The accompanying color photographic illustration shows typical specimens of the foliage and fruit of our new and distinct apriocot variety. The illustration shows the upper and lower surface of the leaves, the exterior and a sectional view of the fruit divided in the suture plane to reveal flesh coloration, and the pit cavity and a stone remain in place. The photographic illustration was taken shortly after being picked (firm ripe) and the colors are as nearly true as is reasonably possible in a color representation of this type.

DESCRIPTION OF THE VARIETY

The following is a detailed botanical description of the present new variety of apricot tree, its flowers, foliage and fruit as based on observation of speciments grown in our experimental orchard located near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Semi-spreading.
- *Production.*—Productive.
- *Bearing.*—Regular.
- *Density.*—Medium dense.

Trunk:
- *Size.*—Stocky.
- *Texture.*—Shaggy.
- *Color.*—Brown to grayish brown (5-E-5) to (5-E-8).

Branches:
- *Size.*—Medium.
- *Texture.*—Smooth to medium rough, varies with maturity.
- *Lenticels.*—Medium number. Small to medium size.
- *Color.*—New growth reddish brown. Old growth light brown to brown.

Leaves:
- *Size.*—Large. Average length — 5". Average width — 2⅞".
- *Form.*—Ovate. Pointed.
- *Texture.*—Smooth.
- *Thickness.*—Medium.
- *Margin.*—Serrate.
- *Petiole.*—Medium length (average 1½"). Medium thickness.
- *Glands.*—Number varies from 2 to 4. Average number 3. Located on base of leaf blade, and upper portion of petiole.
- *Color.*—Upper surface green to dark green (27-F-8) to (28-F-8). Lower surface grayish green to green (28-E-5) to (28-E-7).

Flower buds:
- *Size.*—Medium to large.
- *Length.*—Medium.
- *Form.*—Plump.

Flowers:

*Blooming period.*—Date of first bloom: Feb. 26, 1994. Date of full bloom: Mar. 3, 1994. Varies slightly with climatic conditions.

*Size.*—Large.

*Color.*—Pink, fades to nearly white at petal fall.

*Pollen.*—Present.

Fruit:

*Maturity when described.*—Firm ripe.

*Date of first picking.*—Aug. 15, 1994.

*Date of last picking.*—Aug. 18, 1994.

*Size.*—Large. Average diameter axially 2⅜". Average transversely in suture plane 2⅜". Average measured to right angles in suture plane 2".

*Form.*—Nearly Globose, slightly compressed toward suture plane.

*Suture.*—Shallow but pronounced, extends from base to apex.

*Ventral surface.*—Nearly rounded, very slightly lipped.

*Apex.*—Usually retuse, varies from round to retuse.

*Base.*—Retuse.

*Cavity.*—Rounded to slightly elongated in suture plane. Average depth 3/16". Average breadth ⅜".

Flesh:

*Ripens.*—Evenly.

*Texture.*—Firm.

*Juice.*—Moderate.

*Fibers.*—Small, tender.

*Flavor.*—Good.

*Aroma.*—Moderate.

*Eating quality.*—Good.

*Color.*—Golden yellow to light orange (5-B-5) to (5-B-8).

Skin:

*Thickness.*—Medium.

*Texture.*—Medium, tenacious to the flesh.

*Tendency to crack.*—None.

*Down.*—Scant, very short.

*Color.*—Apricot yellow to golden yellow (5-B-5) to (5-B-8).

Stone:

*Type.*—Freestone.

*Size.*—Medium. Average length 1¼". Average width 1". Average thickness ⅝".

*Form.*—Ovoid.

*Base.*—Mostly straight, some rounded.

*Apex.*—Nearly rounded.

*Sides.*—Equal to unequal.

*Surface.*—Slightly pitted throughout.

*Ridges.*—Distinct ridges extending across surface of stone on both sides of suture plane. Small minor ridges near apex and base.

*Color.*—Light brown to brown (5-D-5) to (5-D-8).

Use: Dessert.

*Market.*—Local and long distance.

Keeping quality: Good.

Shipping quality: Good.

The present new variety of apricot tree, its flowers, foliage and fruit described above may vary in slight detail due to variations in climate, soil conditions and cultural practices under which the variety may be grown; the present description is that of the variety grown under the ecological conditions prevailing near Modesto, Calif.

We claim:

1. A new and distinct variety of apricot tree, substantially as illustrated and described, characterized by its large size, vigorous, semi-spreading growth and being a productive and regulaar bearer of large, yellow-flesh freestone fruit with good flavor and eating quality; the fruit is further characterized by being relatively uniform in ripening throughout the tree, having a high degree of soluble solids (average 16% Brix), having firm flesh with good handling and shipping quality, and ripening in the late maturity season.

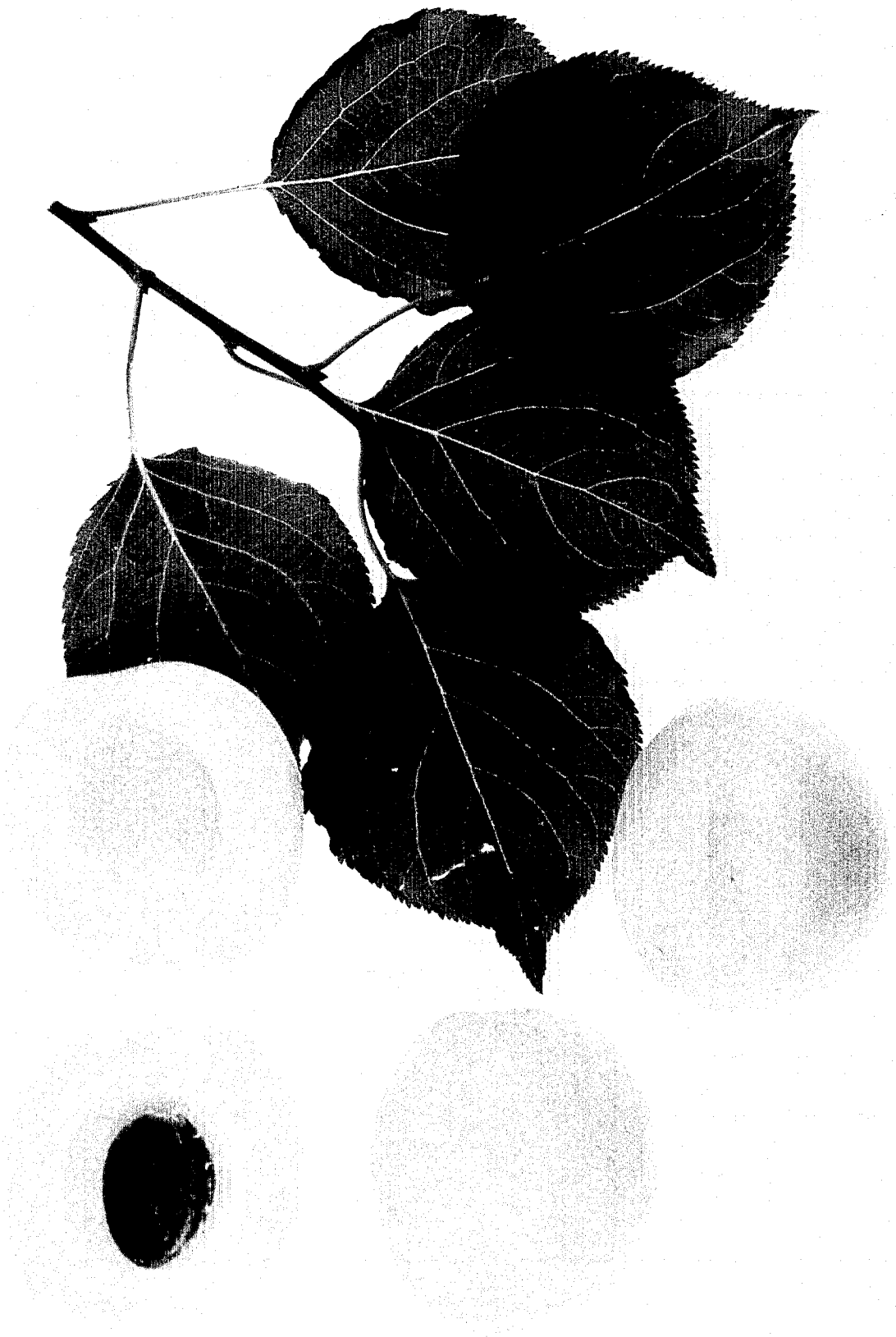

* * * * *